(12) United States Patent
Torsti et al.

(10) Patent No.: US 8,280,003 B2
(45) Date of Patent: Oct. 2, 2012

(54) METHOD FOR CALCULATING HEAD SCATTER PHASE SPACE FOR RADIATION TREATMENT USING A MULTI-LEAF COLLIMATOR WITH DYNAMIC JAWS

(75) Inventors: Tuomas Torsti, Espoo (FI); Sami Siljamaki, Helsinki (FI); Esa Kuusela, Espoo (FI); Laura Korhonen, Espoo (FI)

(73) Assignee: Varian Medical Systems International AG, Zug (CH)

( * ) Notice: Subject to any disclaimer, the term of this patent is extended or adjusted under 35 U.S.C. 154(b) by 270 days.

(21) Appl. No.: 12/830,076

(22) Filed: Jul. 2, 2010

(65) Prior Publication Data

US 2011/0293071 A1 Dec. 1, 2011

Related U.S. Application Data

(60) Provisional application No. 61/349,631, filed on May 28, 2010.

(51) Int. Cl.
*A61N 5/10* (2006.01)

(52) U.S. Cl. .............................................. 378/65; 378/64
(58) Field of Classification Search ............... 378/64–65
See application file for complete search history.

(56) References Cited

U.S. PATENT DOCUMENTS

| 2009/0041200 A1* | 2/2009 | Lu et al. ........................ 378/152 |
| 2011/0091014 A1* | 4/2011 | Siljamaki et al. ............... 378/65 |

* cited by examiner

*Primary Examiner* — Hoon Song

(57) ABSTRACT

A method is proposed for accurate and efficient modeling of head scatter phase space for treatments with dynamic jaws. Specifically, the method enables the efficient calculation of the head scatter phase space in case of a dynamic treatment where jaws and MLC leaves move during the delivery. In one embodiment, the invention can be used to calculate the head scatter contribution during final dose calculation of dynamic treatments. This novel method also enables an accurate calculation of the head scatter contribution from optimal fluence and from jaw positions without having to calculate the leaf sequence. In this embodiment, the invention can be used in optimization of large field IMRT treatments.

20 Claims, 9 Drawing Sheets

METHOD FOR CALCULATING HEAD SCATTER PHASE SPACE FOR RADIATION TREATMENT USING A MULTI-LEAF COLLIMATOR WITH DYNAMIC JAWS

CLAIM OF PRIORITY

This application claims priority to provisional patent application entitled "Method For Calculating Head Scatter Phase Space For Radiation Treatment Using A Multi-Leaf Collimator With Dynamic Jaws," application No. 61/349,631 filed on May 28, 2010.

TECHNICAL BACKGROUND

Radiation therapy (RT) is a popular and efficient method for cancer treatment, where ionizing radiation is used in an attempt to kill malignant tumor cells or to slow down their growth. RT is often combined with surgery, chemotherapy, or hormone therapy, but may also be used as a primary therapy mode. Radiation therapy may be administered as internal RT or brachytherapy or, more commonly, external beam RT.

Internal RT treatment typically includes placing one or more radioactive sources near a designated treatment area, either permanently or temporarily. Conversely, external beam RT typically involves directing radiation beams produced by sources located externally with respect to the patient or radiation subject to the afflicted treatment area. The beam can consist of photons, electrons, protons or other heavy ions; photons being (at present) the most commonly used particle type. Malignant cells are damaged by the ionizing radiation used during the RT. However, the damage from the radiation is not limited to malignant cells and thus, the dosage of radiation to healthy tissues outside the treatment volume is ideally minimized to avoid being similarly damaged.

The development of medical linear accelerators (linacs) have dramatically increased the practicality and efficiency of multi-field RT treatments. Even more recently, computer-controlled hardware such as the multi-leaf collimator (MLC) have been developed that deliver fields conforming to the projection of the target with even greater ease. In more advanced applications, the individual leaves of the MLC are moved separately under computerized control at desired speeds during periods of radiation (e.g., beam-on). This has enabled the generation of spatially modulated radiation fields, since each leaf attenuates the beam for a different time period. The resulting intensity modulated radiotherapy (IMRT) has allowed the application of high dose volumes that conform more closely to the shape of complicated targets. The further integration of x-ray image receptors to the linac has enabled the imaging of the patient before each treatment session and the tracking of tumor motion during treatment delivery. These so-called image-guided RT methods have improved subject positioning accuracy, and have lead to techniques for restricting tumor motion during treatment.

The purpose of traditional RT treatment planning methodologies is to devise a treatment regimen which produces as uniform a dose distribution as possible to the target volumes whilst minimizing the dosage outside this volume. It is crucial to successful radiation therapy that the discrepancies between dose distributions calculated at the treatment planning stage and those delivered to the patient are minimized. Thus, calculating precise levels of radiation at the treatment planning stage is of utmost importance. In conventional radiation therapy treatment planning systems, the radiation is calculated first in the geometry of the particular radiation source (e.g., external or internal), followed by tracking the transport and energy deposition in the particular target volume and/or area of interest.

In radiation therapy, the distribution of particles emanating from a treatment unit given on a plane (e.g. orthogonal to the central axis) is defined as phase-space. At each pixel on the plane, the distribution of each particle type in energy and direction of propagation is given. Conventionally, the primary radiation beam entering the patient (the primary component of the phase space) is often expressed using a two dimensional energy fluence array together with an energy spectrum. The energy spectrum describes the distribution of the beam energy to different energy ranges. In a general case, the energy spectrum also varies spatially within the beam. While the primary photon beam accounts for the vast majority of the energy fluence that enters the patient, there may be other additional contributions as well. Scattered photons may originate from the primary collimator and the flattening filter. In addition, electrons produced in the air as well as other parts of the accelerator may also contaminate the beam. These scattered photons may, in the aggregate, detrimentally affect the accuracy of a calculated dosage, if they are not modeled in the calculation. In order to model the effect of the scattered photons, the phase space of the scattered photons must be modeled separately to more accurately determine the total phase space of the radiation beam.

Unfortunately, the phase-space of the scattered photons cannot be accurately described using a two-dimensional energy fluence, because the energy fluence passing through a plane orthogonal to the beam axis depends on the distance from the target in a non-trivial way (or equivalently, not all scattered photons are traveling in a line emanating from the primary source). One solution to this problem is to use a plurality of two-dimensional energy fluences at different distances from the target (a 3D-fluence) to model the head scatter phase space. For a static beam (when neither the MLC nor collimator jaws move), the 3D energy fluence can be calculated by tracing the ray from a two-dimensional source located in the treatment head (e.g. at the bottom level of the flattening filter), taking into account the positions of the collimating jaws and the opening ratio matrix (ORM) defined by the MLC leaves.

During the delivery of an intensity modulated radiotherapy (IMRT) treatment, the MLC leaves, the collimator jaws, or both may be moving. In typical treatment planning systems this motion is represented using a plurality of control points. These control points also control the movement of the corresponding components of the linac. Under these circumstances, the 3D-fluence should (in principle) be calculated for each control point. However, if the jaws are static and only the MLC leaves move, an adequate approximation can be obtained by only using the two-dimensional ORM of the primary photon beam and the static jaw positions as input. However, if the jaws also move, it is necessary to calculate the 3D fluence for a plurality of jaw positions. There can be several hundred jaw positions in the set of control points for a typical clinical IMRT field. Such a field may consist of multiple static segments or it may be a sliding window beam with jaw-tracking. Unfortunately, calculating the 3D-fluence for each of these jaw positions can be extremely time consuming, and will result in a much longer dose calculation time. In addition, there is currently no simple way to deduce an ORM of the MLC separately for each jaw-opening based on the total ORM of the control point sequence only.

Under conventional techniques, the contribution of head scatter has been calculated either in a very approximate manner (using a single jaw-opening) or using a very CPU-intensive (slow) method (using all jaw-openings). Under such techniques, using the single-jaw-opening for a head-scatter contribution calculation is very likely to decrease the accuracy of the dose calculation, often significantly. On the other hand, calculating the contribution of head scatter by using every jaw-opening results in a higher degree of accuracy, but can be very time and resource intensive, resulting in inefficient processing.

SUMMARY

This Summary is provided to introduce a selection of concepts in a simplified form that is further described below in the Detailed Description. This Summary is not intended to identify key features or essential features of the claimed subject matter, nor is it intended to be used to limit the scope of the claimed subject matter.

A method is proposed for accurate and efficient modeling of head scatter phase space for treatments with dynamic jaws. Specifically, the method enables the efficient calculation of the head scatter phase space in case of a dynamic treatment where jaws and MLC leaves move during the delivery, but the gantry is static. Examples of such treatments are 1) an IMRT delivery with multiple carriage groups. 2) an IMRT delivery with multiple static segments and 3) jaw-tracking sliding window IMRT delivery. This novel method enables an accurate calculation of the head scatter contribution from optimal fluence together with known jaw positions without having to calculate the leaf sequence. In this embodiment, the invention can be used in optimization of large field IMRT treatments.

The calculation algorithm for the 3D head scatter fluence requires a jaw-opening and a two-dimensional ORM as input. Several such 3D-fluences can be added together. A clustering method is used to create a small number of jaw-opening sets (JOSs) from the possibly large number of jaw-openings composing the dynamic treatment. In each set all jaw-openings are close to each other, with respect to a distance measure. For example, the non-overlapping area of two jaw-openings can be used as a distance measure. Each JOS is accompanied with a representative jaw-opening. For example, if a jaw-opening is defined by a quadruplet (X1, X2, Y1, Y2) i.e. positions of the left and right X and Y jaw, the arithmetic average of all quadruplets belonging to the JOS can be used. Each JOS also may be accompanied by a two-dimensional MLC fluence (ORM) in order to calculate its contribution to the 3D-fluence.

If the full leaf sequence is available, it is possible to calculate an accurate two-dimensional ORM for each JOS. However when the full leaf sequence is not easily available, or when calculating the accurate two-dimensional ORM for each JOS is too expensive, the partial ORM for each JOS may be deduced from the total two-dimensional ORM. Each pixel of the total primary two-dimensional ORM belongs to a number of representative jaw-openings. Each JOS has an associated weight determined by the sum of the generated monitor units (MUs) of the associated control points. The pixel value is distributed to the partial ORMs of the JOSs proportionally to their MU weights. In the method above, each pixel either belongs to a JOS representative jaw-opening or not. The method can be extended, by associating each pixel with a continuous weight that has value of one within the representative jaw-opening and decrease e.g. exponentially as a function of the distance from the edge of the jaw-opening. This weight is multiplied by the MU weight when determining the decomposition of ORMs.

BRIEF DESCRIPTION OF DRAWINGS

The accompanying drawings, which are incorporated in and form a part of this specification, illustrate embodiments of the invention and, together with the description, serve to explain the principles of the invention.

DETAILED DESCRIPTION

Figure 1:
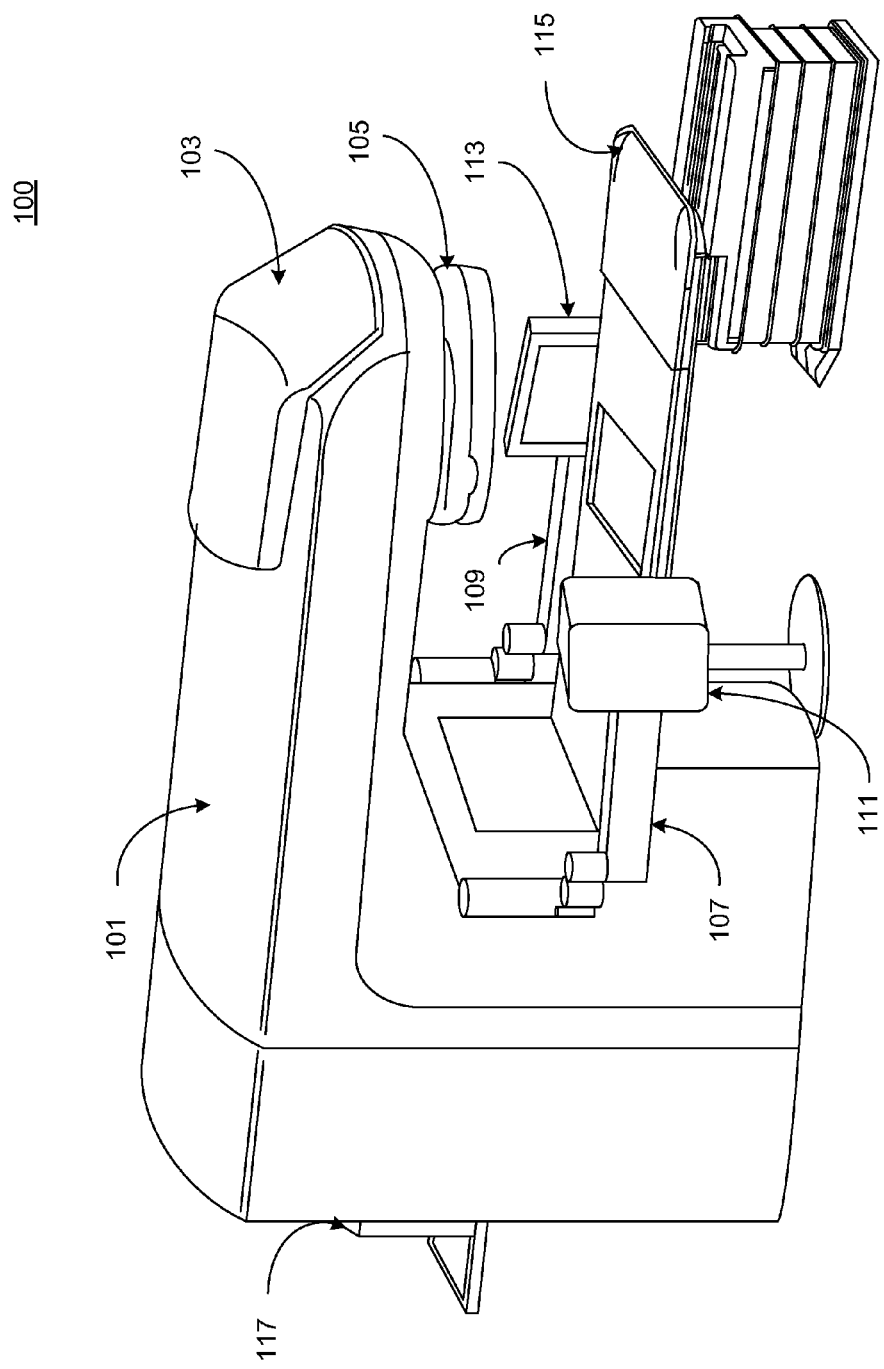
FIG. 1 depicts an illustration of an exemplary radiation therapy and imaging device, in accordance with embodiments of the present invention.

Reference will now be made in detail to several embodiments. While the subject matter will be described in conjunction with the alternative embodiments, it will be understood that they are not intended to limit the claimed subject matter to these embodiments. On the contrary, the claimed subject matter is intended to cover alternative, modifications, and equivalents, which may be included within the spirit and scope of the claimed subject matter as defined by the appended claims.

Furthermore, in the following detailed description, numerous specific details are set forth in order to provide a thorough understanding of the claimed subject matter. However, it will be recognized by one skilled in the art that embodiments may be practiced without these specific details or with equivalents thereof. In other instances, well-known methods, procedures, and components, have not been described in detail as not to unnecessarily obscure aspects and features of the subject matter.

Portions of the detailed description that follows are presented and discussed in terms of a method. Although steps and sequencing thereof are disclosed in figures herein (e.g., FIGS. 3, 5, 6, 7, and 8) describing the operations of this method, such steps and sequencing are exemplary. Embodiments are well suited to performing various other steps or variations of the steps recited in the flowchart of the figure herein, and in a sequence other than that depicted and described herein.

Embodiments described herein may be discussed in the general context of computer-executable instructions residing on some form of computer-usable medium, such as program modules, executed by one or more computers or other computing devices. Generally, program modules include routines, programs, objects, components, data structures, etc., that perform particular tasks or implement particular abstract data types. The functionality of the program modules may be combined or distributed as desired in various embodiments.

By way of example, and not limitation, computer-usable media may comprise computer storage media and communication media. Computer storage media includes volatile and nonvolatile, removable and non-removable media implemented in any method or technology for storage of information such as computer-readable instructions, data structures, program modules or other data. Computer storage media includes, but is not limited to, random access memory (RAM), read only memory (ROM), electrically erasable programmable ROM (EEPROM), flash memory or other memory technology, compact disk ROM (CD-ROM), digital versatile disks (DVDs) or other optical storage, magnetic cassettes, magnetic tape, magnetic disk storage or other magnetic storage devices, or any other medium that can be used to store the desired information.

Communication media can embody computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency (RF), infrared and other wireless media. Combinations of any of the above should also be included within the scope of computer-readable media.

Exemplary Radiation Treatment and Imaging Machine

With reference now to FIG. 1, an illustration of an exemplary radiation therapy and imaging device 100 is depicted, in accordance with one embodiment. In one configuration, radiation therapy and imaging device 100 includes a support structure (e.g., gantry 101), a therapeutic radiation source 103 (e.g., a medical linear accelerator) including a treatment head 105, a plurality of robotic arms (e.g., robotic arms 107, 109), a diagnostic radiation source 111, a diagnostic radiation imager 113, and a patient couch 115. In some embodiments, radiation therapy device 100 may include a communicatively coupled computing device 117 for calculating dosages and processing images.

In one embodiment, the end of gantry 101 positioned above patient couch 115 is attached to a therapeutic radiation source 103. While receiving treatment, a patient is positioned (typically supine) on patient couch 115. A target volume (generally disposed within or about the patient subject) is acquired. According to one embodiment, the target volume is acquired by generating a volumetric image of the area within the patient. A volumetric image of the area is acquired by, for example, generating a three dimensional image using diagnostic radiation source 111 in conjunction with diagnostic radiation imager 113. The imaging generated from the diagnostic radiation process may be subsequently utilized to provide targeting information which can be used to accurately direct the therapeutic radiation from therapeutic radiation source 103 to the target volume from various angles.

Exemplary Medical Linear Accelerator

Figure 2:
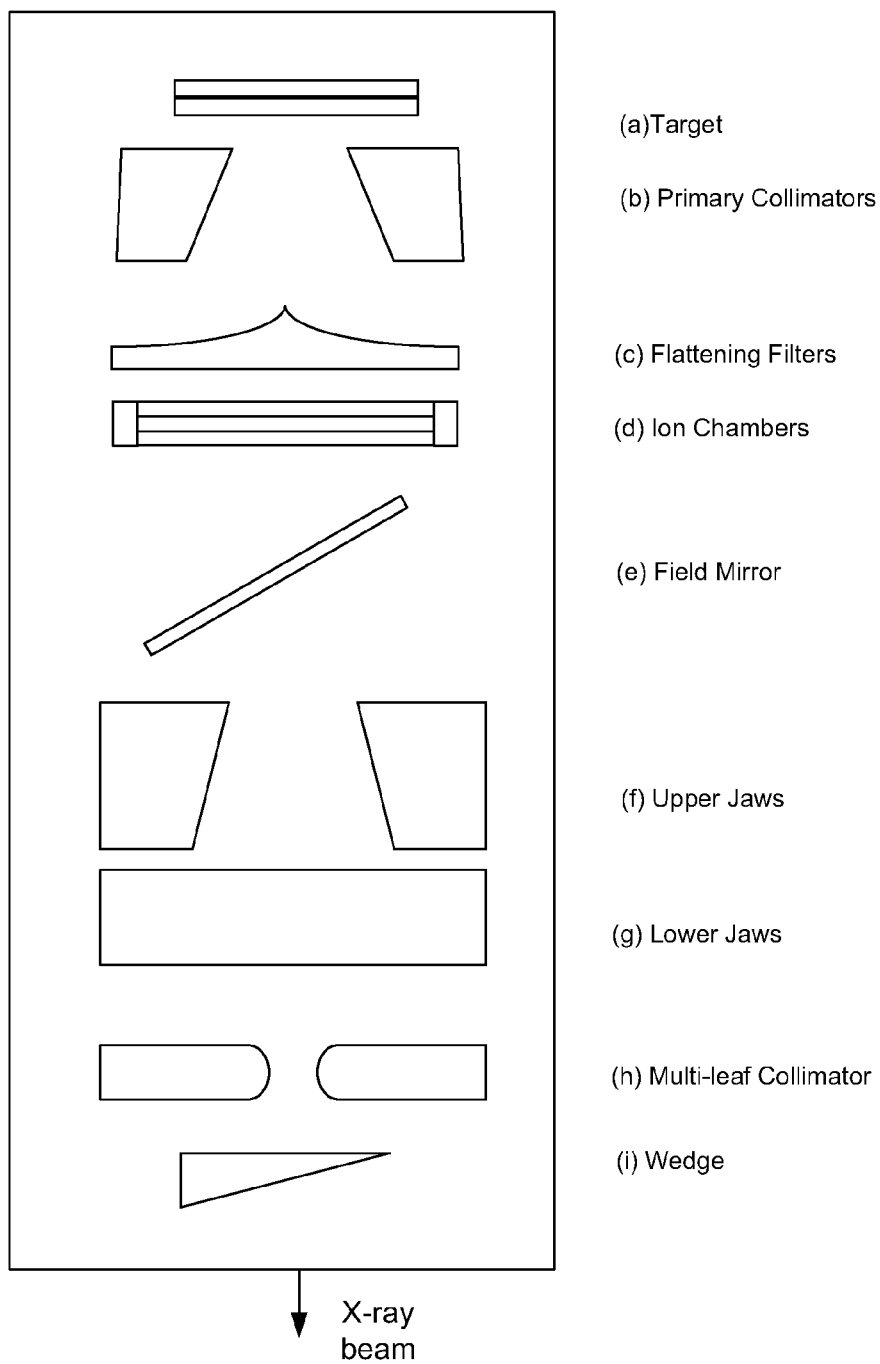
FIG. 2 depicts an illustration of an exemplary treatment head of a medical linear accelerator, in accordance with embodiments of the present invention.

With reference now to FIG. 2, an illustration of an exemplary treatment head 200 of a medical linear accelerator is depicted, in accordance with one embodiment. As presented, the treatment head 200 receives a primary electron beam, applied to a target (a) to generate photons that comprise the radiation treatment. The photons are further modified (attenuated, directed) by a plurality of components (b)-(i). In one configuration, after an accelerated primary electron beam emerges from a source (e.g., an electron gun), the electron beam will hit a target (a), commonly consisting of a high-Z metal, after which the electrons will produce what are referred to as "bremsstrahlung photons" (photon beam).

The primary photon beam is subsequently collimated initially by a primary collimator (b) and the photon fluence is differentially attenuated by a flattening filter (c) to produce a reasonably flat dose distribution. Next, a monitor ion chamber (d) and field mirror (e) monitor the radiation by generating monitor units to correspond to detected primary photons passing through the monitor chamber (e.g., 97-100% of the signal, depending on field size) and backscattered photons (e.g., the remaining 0-3% of the signal) of the primary photon beam when particles of the photon beam are intersected by the placement beam collimating and/or modulating devices (e.g., jaws, MLC leaves). Finally the photon beam is shaped and modulated by various devices such as jaws (including an upper jaw (f) and a lower jaw (g), multi-leaf collimators (MLC) (h), and/or wedges and blocks (i), etc.

According to embodiments of the present invention, the photon beam is modulated over a series of control points, which may consist of varying positions of the jaws and the leaves of the MLC. The three-dimensional head scatter fluence from such a configuration may be accurately derived according to a method of aggregating the positions of the jaws with other, proximate jaw positions. When the positions of the MLC leaves are known (e.g., from a leaf sequence), the three-dimensional fluence may be derived from a plurality of statically positioned jaws (e.g., the jaw-opening sets) rather than the entire collection of control points. This approach allows a much higher degree of accuracy than deriving a three-dimensional head scatter fluence from a single static jaw position while eliminating a majority of the calculation time necessary to calculate separate 3D fluences for an entire set of control points, which may, in some procedures, reach or even exceed five hundred.

Three Dimensional Fluence Calculation

Figure 3:
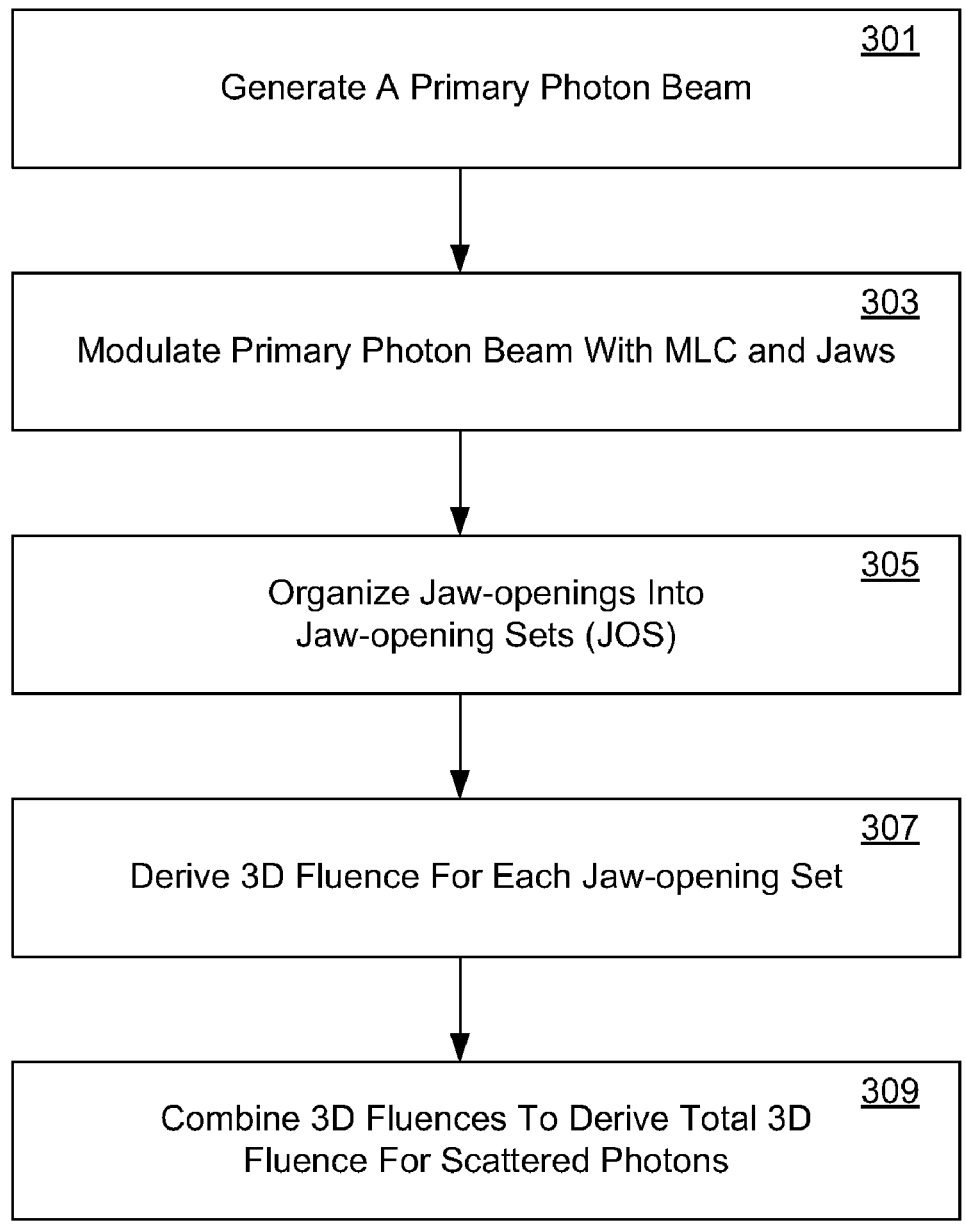
FIG. 3 depicts flowchart of one embodiment of a method for efficiently calculating a three dimensional head scatter fluence generated by a radiation therapy device, in accordance with embodiments of the present invention.

FIG. 3 is a flowchart 300 of one embodiment of a method for efficiently calculating a three dimensional head scatter fluence generated by a radiation therapy device, in accordance with one embodiment. Specifically, the method enables the efficient calculation of the 3D fluence in the case of a dynamic treatment where jaws and MLC leaves move during the delivery, but the gantry is static. Examples of such treatments are 1) an IMRT delivery with multiple carriage groups. 2) an IMRT delivery with multiple static segments and 3) jaw-tracking sliding window IMRT delivery.

In one embodiment, this 3D head scatter fluence can be used during the calculation of final dose for a treatment plan. The final dose calculation also needs to take into account the other major components of the radiation beam, such as the primary radiation and electron contamination. In another embodiment, this method may be used to derive an accurate calculation of the head scatter contribution from optimal fluence from multiple jaw positions without having to calculate the leaf sequence. In this embodiment, the invention can be used in optimization of large field IMRT treatments. Steps 301-309 describe exemplary steps comprising the process depicted in flowchart 300 in accordance with the various embodiments herein described. In one embodiment, the flowchart 300 is implemented as computer-executable instructions stored in a computer-readable medium.

At step 301, a primary photon beam is generated. The primary photon beam may be generated by, for example, applying an electron beam (e.g., generated by an electron gun and accelerated via an accelerating device in a medical linear accelerator) to a metal target (e.g., consisting of a high-Z metal) and generating a beam of bremsstrahlung photons. In further embodiments, once the photon beam has been generated, the beam may be modified by passing the beam through a configuration of modulating and/or particle monitoring devices. Typically, one or more flattening filters, and a primary collimator may be implemented to refine (e.g., attenuate) the photon beam before application to the subject volume (patient). In addition, an ion chamber may be placed within the flow of the directed beam to monitor the radiation generated by the linac (e.g., by generating monitor units).

At step 303, the photon beam is further modulated by focusing the photon beam through particle impeding jaws and a multi-leaf collimator (MLC). According to some radiation therapy treatments, collimation of the photon beam may be performed by positioning the plurality of jaws and the plurality of leaves of the MLC such that most of the particles of the photon beam that hit the collimating devices are absorbed and do not reach the patient. The unimpeded particles comprising the photon beam travel through the openings between the jaws (jaw-openings) and leaves. The radiation treatment can be described using a set of control points, where each control point may comprise the specific positions of the jaws and leaves, and the corresponding monitor unit count. A typical treatment may include potentially hundreds of control points. The positions of the jaw openings and leaves may be expressed as a set of coordinates, for instance.

At step 305, the jaw-openings represented in the one or more control points are organized into one or more jaw-opening sets. In further embodiments, the jaw-openings may be organized into one or more jaw-opening sets based on proximity according to a distance measure in the space of the jaw openings. That is, proximately located jaw-openings may be grouped into the same set. Thus, for example, all jaw-openings within a pre-determined threshold distance may be grouped together in a jaw-opening set. In still further embodiments, each jaw-opening set may include a representative jaw-opening. This representative jaw-opening may consist of an actual jaw-opening within the set, or a virtual jaw-opening calculated as the arithmetic average of the positions of the jaw-openings in the set or by some other suitable manner.

At step 307, a three dimensional (3D) head scatter fluence is derived for the plurality of jaw-opening sets organized in step 305. The 3D head scatter fluence for a jaw-opening set may be calculated by applying an algorithm where the position of the representative jaw-opening of the jaw-opening set and the two-dimensional ORM of the primary photon beam are used as input. Several such 3D-fluences can be combined together at step 309 to derive the total aggregate 3D head scatter fluence for the radiation therapy procedure.

Exemplary Distance Calculation Between Jaw-Openings

Figure 4:
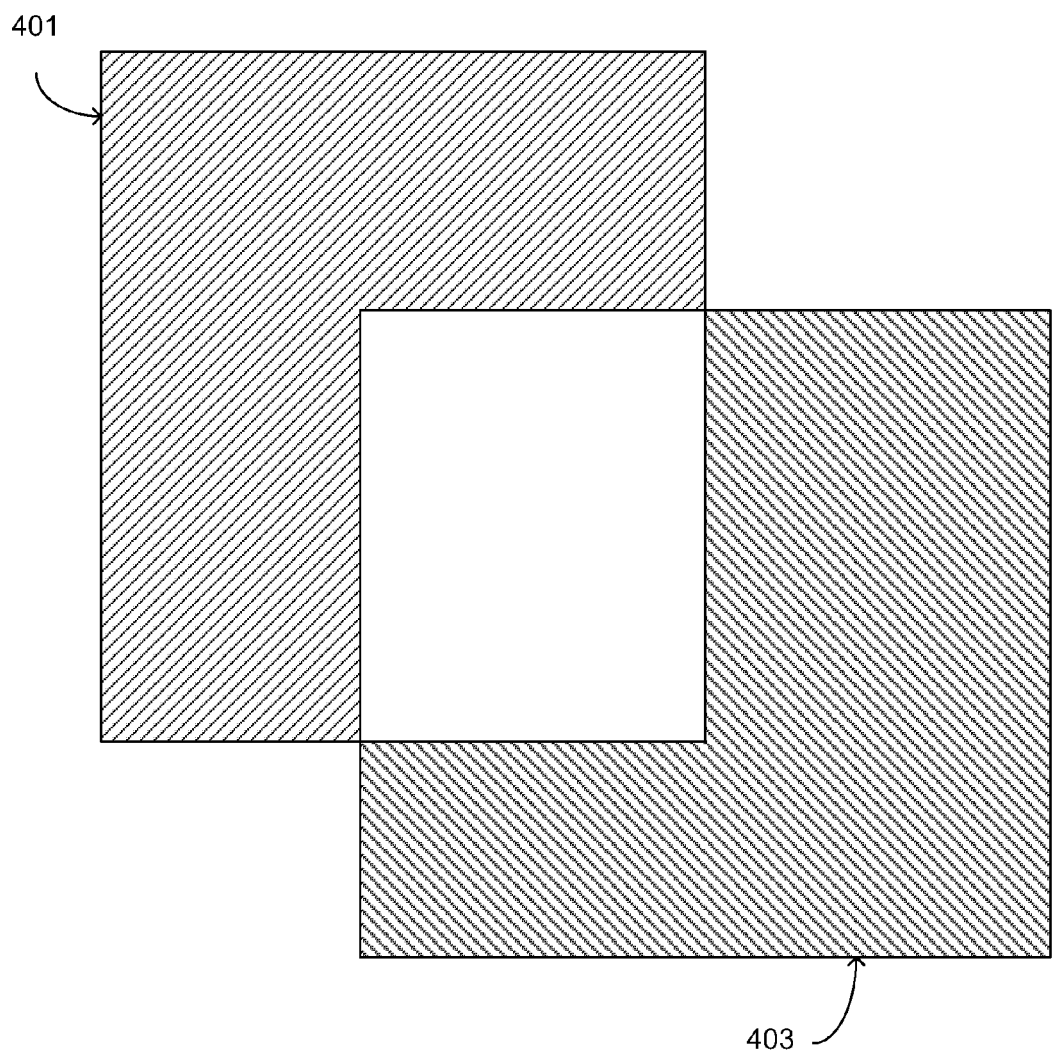
FIG. 4 is an illustration of a technique for determining distance between jaw-openings, in accordance with embodiments of the present invention.

FIG. 4 is an illustration 400 of a technique for determining distance between jaw-openings, in accordance with one embodiment. This technique may be performed, for example, during a process of determining proximate jaw-openings for organization into jaw-opening sets, such as step 305 of the process 300 for calculating three dimensional fluence of head scattered radiation described above with respect to FIG. 3. As depicted in FIG. 4, control points during a treatment application procedure may include corresponding jaw-openings (e.g., jaw-opening 401, 403). These jaw-openings may, for example, represent the space disposed between two jaws in a control point.

Each control point of a treatment is associated with a set of jaw positions. In some instances, these positions may overlap with the jaw-opening positions of other control points. This is depicted as the overlap 405 between jaw-opening 401 and 403 of FIG. 4. In one embodiment, determining the distance between jaw-openings may be performed by calculating the overlapping intersections shared between any two or more jaw-openings. Thus, for example, jaw-openings with a common intersection above a threshold area may be determined to be proximately disposed with respect to each other and grouped within the same jaw-opening set. Conversely, jaw-openings with no common intersection or a common intersection having an area below a threshold may be determined to be insufficiently proximate to be grouped within the same jaw-opening set. According to such embodiments, the threshold may be pre-determined. In further embodiments, a jaw-opening (and its corresponding control point(s)) may be a member of multiple jaw-opening sets.

Calculation of Jaw-Opening Set Specific Three Dimensional Fluence

Figure 5:
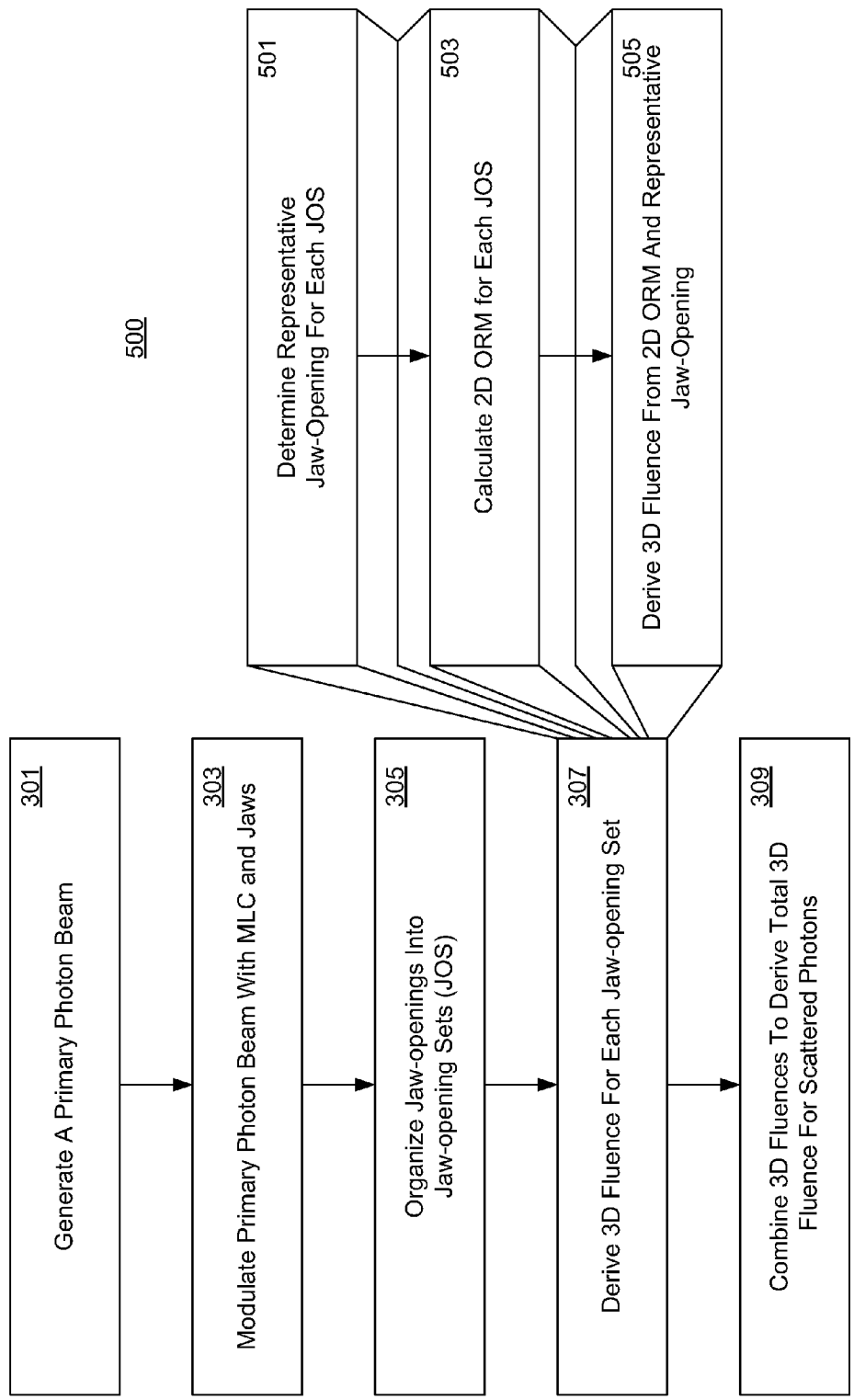
FIG. 5 depicts a flowchart of one embodiment of a method for calculating 3D head scatter fluence generated by a radiation therapy device for a jaw-opening set, in accordance with embodiments of the present invention.

FIG. 5 is a flowchart 500 of one embodiment of a method for calculating 3D head scatter fluence generated by a radiation therapy device for a jaw-opening set, in accordance with one embodiment. The method may be performed, for example, after the process of determining proximate jaw-openings for organization into jaw-opening sets, such as at step 305 of the process 300 for calculating three dimensional fluence of head scattered radiation described above with respect to FIG. 3. Steps 501-505 describe exemplary steps comprising the process depicted in flowchart 500 in accordance with the various embodiments herein described. In one embodiment, the flowchart 500 is implemented as a portion of the computer-executable instructions for executing the method of flowchart 300 and stored in a computer-readable medium.

At step 501, the position of the representative jaw-opening for the jaw-opening set is determined. Determining the position of the representative jaw-opening may be performed by, for example, averaging the positions in space of the jaw-openings comprised in the jaw-opening set. At step 503, a two-dimensional (2D) opening-ratio matrix of a jaw-opening set is calculated. In one embodiment, the jaw-opening set comprises one or more jaw-openings corresponding to a set of control points for a radiation treatment. Finally, at step 505, a 3D fluence corresponding to the jaw-opening set is derived from the position of the representative jaw-opening and the 2D fluence of the primary photon beam. According to some embodiments, the 3D fluence for the jaw-opening set may be calculated using an algorithm having as input the position of a static jaw-opening (the representative jaw-opening), and the opening ratio matrix of the leaves of the multi-leaf collimator.

Calculation of Jaw-Opening Set Specific Two Dimensional Opening-Ratio Matrix

Figure 6:
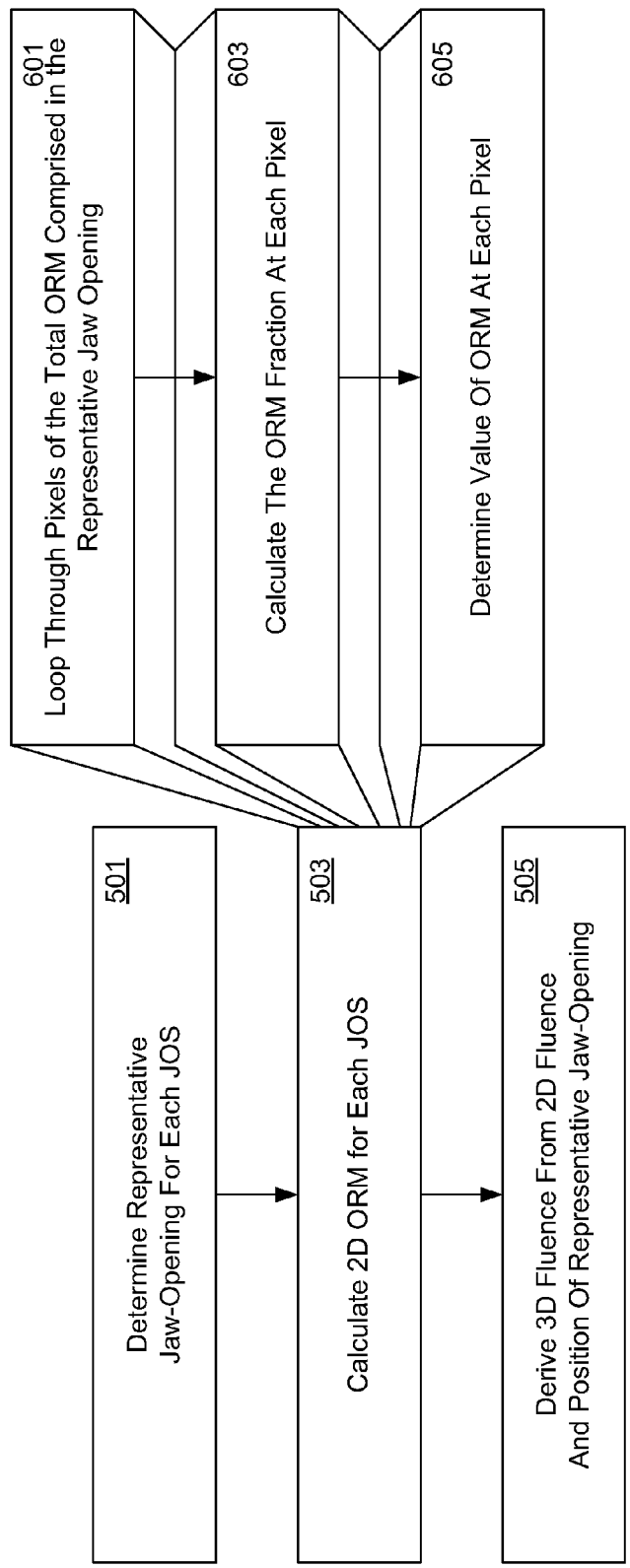
FIG. 6 depicts a flowchart of one embodiment of a method for calculating a 2D partial opening ratio matrix generated by a radiation therapy device for a jaw-opening set, in accordance with embodiments of the present invention.

FIG. 6 is a flowchart 600 of one embodiment of a method for calculating a 2D opening-ratio matrix generated by a radiation therapy device for a jaw-opening set, in accordance with one embodiment. The method may be performed, for example, during a process of calculating 2D head scatter fluence for a jaw-opening set, such as at step 503 of the process 500 for calculating two dimensional fluence of a specific jaw-opening set described above with respect to FIG. 5. Steps 601-605 describe exemplary steps comprising the process depicted in flowchart 600 in accordance with the various embodiments herein described. In one embodiment, the flowchart 600 is implemented as a portion of the computer-executable instructions for executing the method of flowchart 300 and stored in a computer-readable medium.

According to some embodiments, an opening-ratio matrix may be implemented to comprise a plurality of pixels. Under such implementations, the pixels of a total opening-ratio matrix may correspond with a representative jaw-opening of a jaw-opening set. In one embodiment, the pixels of the total ORM that are disposed within the representative jaw opening of a JOS of interest are determined at step 601.

At step 603, the ORM fraction at each pixel p is calculated. Calculating the fraction of the ORM for a pixel p may be performed by, for example, determining the number of monitor units corresponding to the jaw-openings of a jaw-opening set ($MU_{JOS}$) and determining the number of monitor units of the jaw-opening sets inside which the pixel p is located ($MU_p$). The ORM fraction $f_{JOS,p}$ is defined as $MU_{JOS}/MU_p$. At step 605, the value of the ORM for the JOS of interest at pixel p is calculated as $f_{JOS,p}*ORM_{Total,p}$, where $ORM_{Total,p}$ is the value of the total ORM at pixel p.

In another embodiment of the process 600 the multi-leaf collimator is referenced to determine the positions of the plurality of leaves for the control points corresponding to the jaw-opening set. Then, an opening ratio matrix corresponding to the jaw-opening set is calculated directly from the partial leaf sequence corresponding to the jaw opening set in question.

According to some embodiments, each jaw-opening set may be assigned an associated weight determined by the sum of the monitor units produced at the control points associated with the jaw-opening set. The pixels of the total primary opening-ratio matrix may be subsequently distributed among the partial opening-ratio matrices of the jaw-opening sets proportionally to their generated monitor unit values. According to further embodiments of process 600, the allocation of weighted values may be extended by associating each pixel with a continuous weight (e.g., having a value of one) within the representative jaw-opening which decreases (e.g. exponentially) as a function of the distance from the edge of the jaw-opening. This (proximity) weight is multiplied by the MU weight when determining the allocation of the specific opening-ratio matrices.

Directional Distribution Calculation

In some instances, instead of representing the head scatter phase space using a 3D fluence and a spectrum, it may also be possible to represent the same information through alternative means. In one embodiment, the head scatter phase may be expressed by using a distribution of directions given on a plane perpendicular to the central axis of the linac and a spectrum. In such a representation, the space of possible directions can be described, for instance, by using two angles (e.g., a polar angle $\theta$, and a azimuth angle $\phi$). The range of possible polar and azimuth angles is then divided into a number of discrete bins. The directional distribution may subsequently define the number of particles traveling into each directional bin.

Figure 7:
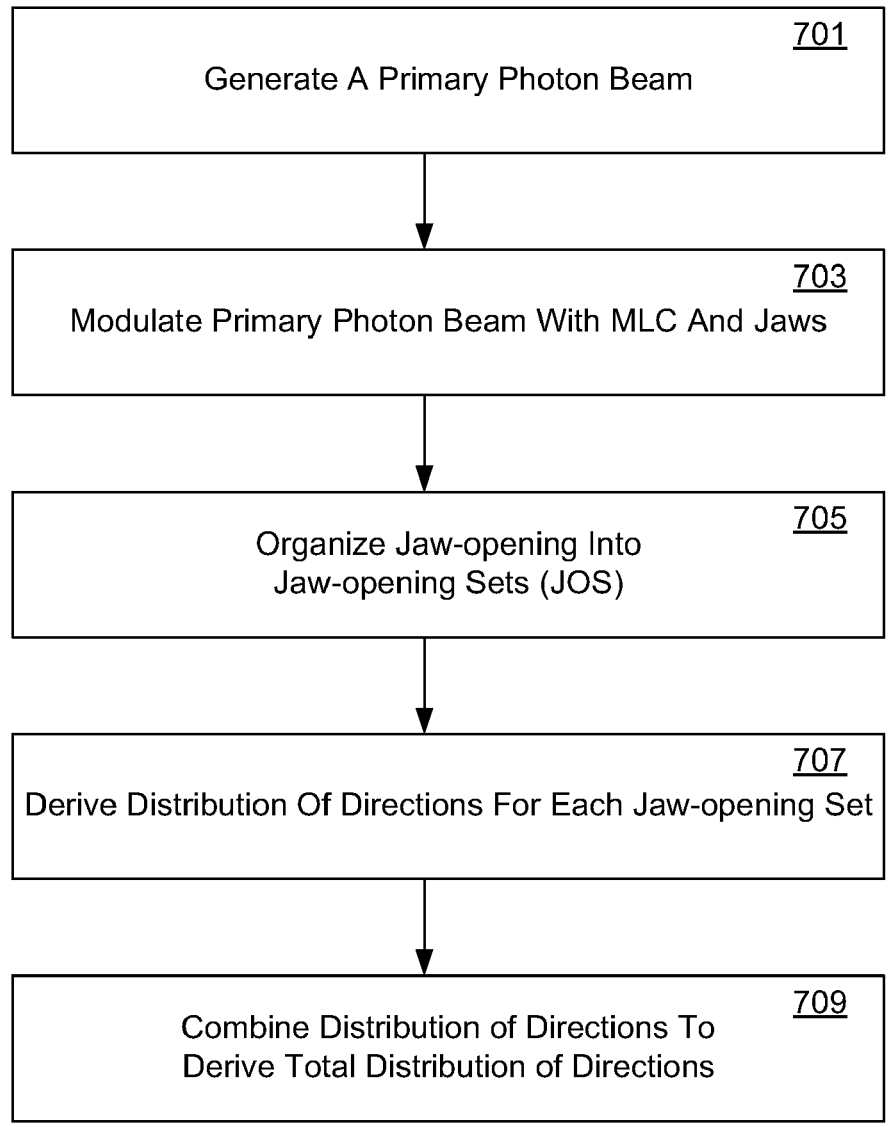
FIG. 7 depicts flowchart of one embodiment of a method for efficiently calculating head scatter phase space from a total distribution of directions, in accordance with embodiments of the present invention.

FIG. 7 is a flowchart 700 of an alternate embodiment of a method for efficiently calculating a head scatter phase space generated by a radiation therapy device, in accordance with one embodiment. Specifically, the method enables the efficient calculation of the distribution of directions for jaw-opening sets instead of 3D fluence. Steps 701-709 describe exemplary steps comprising the process depicted in flowchart 700 in accordance with the various embodiments herein described. In one embodiment, the flowchart 700 is implemented as computer-executable instructions stored in a computer-readable medium. Steps 701-705 correspond to steps 401-405 described above with respect to FIG. 4 and are omitted for the sake of redundancy.

According to one aspect, a distribution of directions can be derived for each JOS at step 707 (rather than the 3D fluence in step 407 of FIG. 4 described above). In one embodiment, the distribution of directions can be derived based on the representative jaw-opening of the jaw-opening set and the 2D partial ORM. Likewise, in lieu of combining the 3D fluences for a plurality of jaw-opening sets in step 409 of FIG. 4, the distribution of directions is cumulatively combined to derive a total distribution of directions at step 709.

Calculation of Jaw-Opening Set Specific Distribution of Directions

Figure 8:
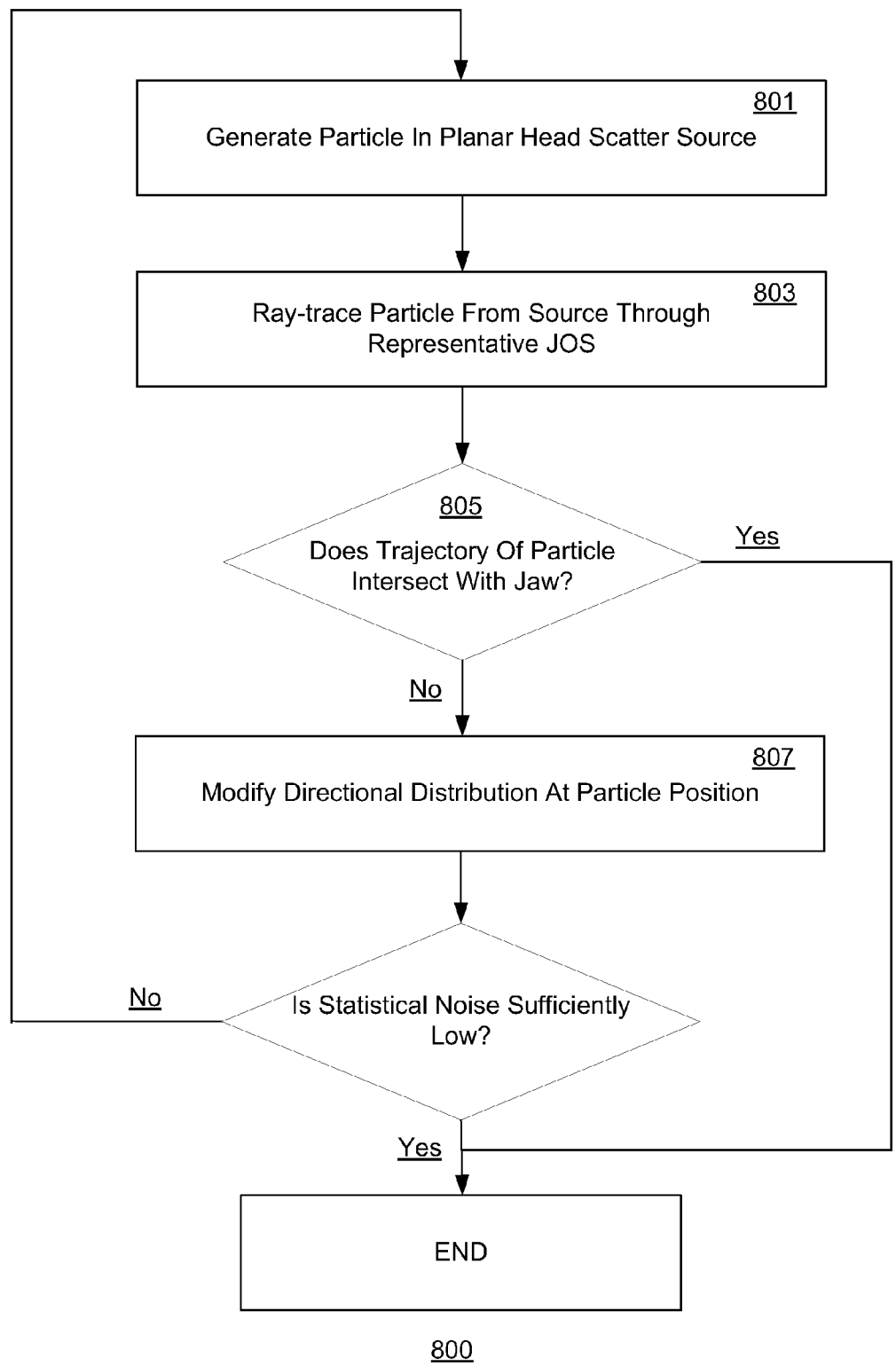
FIG. 8 depicts a flowchart of one embodiment of a method for calculating a distribution of directions for a jaw-opening set, in accordance with embodiments of the present invention.

FIG. 8 is a flowchart 800 of one embodiment of a method for calculating a distribution of directions for a jaw-opening set, in accordance with one embodiment. The method may be performed, for example, after the process of determining proximate jaw-openings for organization into jaw-opening sets, such as at step 705 of the process 700 for calculating a total distribution of directions for representing head scatter phase space described above with respect to FIG. 7. Steps 801-807 describe exemplary steps comprising the process depicted in flowchart 800 in accordance with the various embodiments herein described. In one embodiment, the flowchart 800 is implemented as a portion of the computer-executable instructions for executing the method of flowchart 700 and stored in a computer-readable medium.

As depicted in FIG. 8, the distribution of directions may be derived based on the representative jaw-opening of a jaw-opening set and the 2D partial ORM according to the follow steps. At step 801, a particle from the planar head scatter source located in the treatment unit head is generated. This can be accomplished by sampling a position from a Gaussian distribution on the planar source plane, and the direction angles ($\theta$, $\phi$) such that the particles emitted by the source are distributed uniformly on a sphere.

At step 803, the particle from the planar source is ray-traced through the jaw geometry determined by the representative jaw opening of the JOS. At step 805, an intersection of the particle trajectory with any of the jaws is determined. If the particle trajectory intersects with any of the jaws, the trajectory is stopped. Otherwise, the directional distribution at the position of the particle on the plane is modified at step 807. As a result of the modification performed at step 807, the value at the direction bin corresponding to the particle direction is increased by an amount proportional to the pixel value of the 2D partial ORM at the same position. Where necessary, steps 801-807 may be repeated until the statistical noise level in the distribution of directions on the plane is low enough to comprise a head scatter phase space of sufficient accuracy.

Exemplary Computing Device

Figure 9:
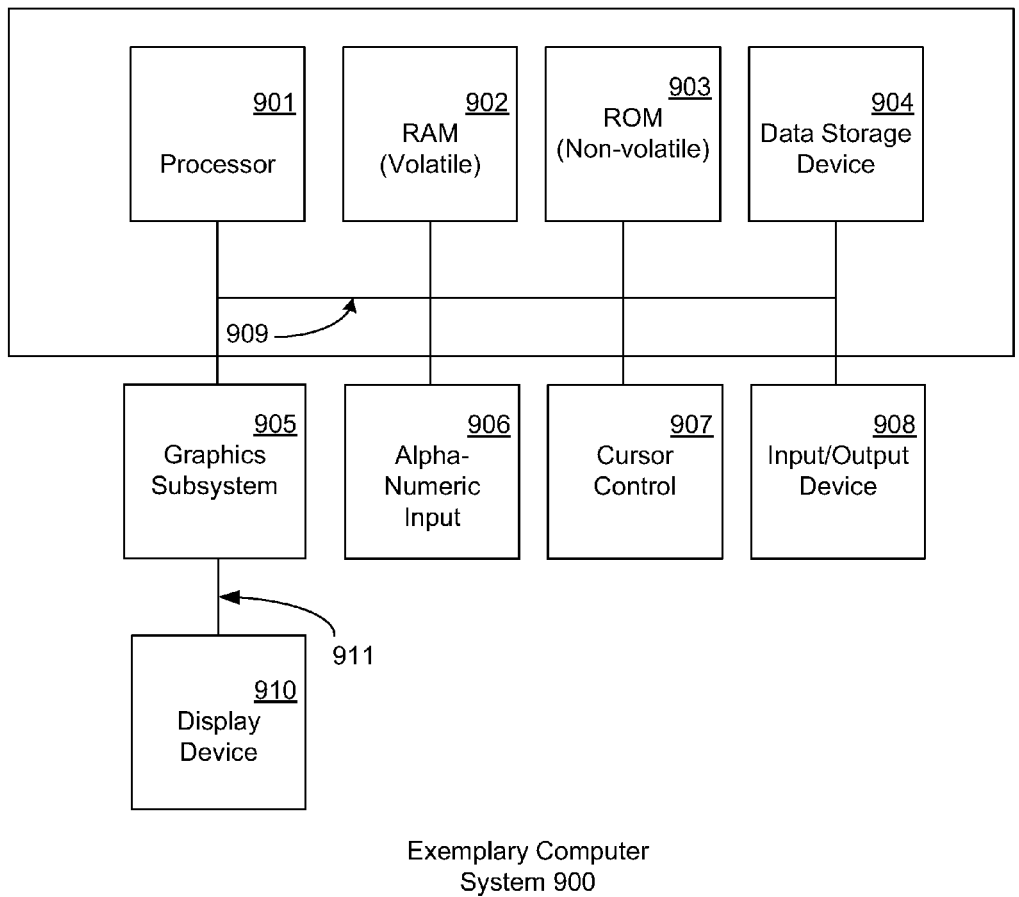
FIG. 9 depicts an exemplary computing environment, in accordance with embodiments of the present invention.

As presented in FIG. 9, an exemplary system upon which embodiments of the present invention may be implemented includes a general purpose computing system environment, such as computing system 900. In its most basic configuration, computing system 900 typically includes at least one processing unit 901 and memory, and an address/data bus 909 (or other interface) for communicating information. Depending on the exact configuration and type of computing system environment, memory may be volatile (such as RAM 902), non-volatile (such as ROM 903, flash memory, etc.) or some combination of the two.

Computer system 900 may also comprise an optional graphics subsystem 905 for presenting information to the computer user, e.g., by displaying information on an attached display device 910, connected by a video cable 911. According to embodiments of the present claimed invention, the graphics subsystem 905 may be coupled directly to the display device 910 through the video cable 911. A graphical user interface of an application for controlling a medical linear accelerator executing in the computer system 900 may be generated in the graphics subsystem 905, for example, and displayed to the user in the display device 910. In alternate embodiments, display device 910 may be integrated into the computing system (e.g., a laptop or netbook display panel) and will not require a video cable 911. In one embodiment, the processes 300, 500, 600, 700, and 800 may be performed, in whole or in part, by graphics subsystem 905 in conjunction with the processor 901 and memory 902, with any resulting output displayed in attached display device 910.

Additionally, computing system 900 may also have additional features/functionality. For example, computing system 900 may also include additional storage (removable and/or non-removable) including, but not limited to, magnetic or optical disks or tape. Such additional storage is illustrated in FIG. 9 by data storage device 907. Computer storage media includes volatile and nonvolatile, removable and non-removable media implemented in any method or technology for storage of information such as computer readable instructions, data structures, program modules or other data. RAM 902, ROM 903, and data storage device 907 are all examples of computer storage media.

Computer system 900 also comprises an optional alphanumeric input device 906, an optional cursor control or directing device 907, and one or more signal communication interfaces (input/output devices, e.g., a network interface card) 909. Optional alphanumeric input device 906 can communicate information and command selections to central processor 901. Optional cursor control or directing device 907 is coupled to bus 909 for communicating user input information and command selections to central processor 901. Signal communication interface (input/output device) 909, also coupled to bus 909, can be a serial port. Communication interface 909 may also include wireless communication mechanisms. Using communication interface 909, computer system 900 can be communicatively coupled to other computer systems over a communication network such as the Internet or an intranet (e.g., a local area network), or can receive data (e.g., a digital television signal).

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A method for calculating three dimensional head scatter fluence of a radiation treatment beam, the method comprising:
   generating a primary photon beam, the primary photon beam producing scattered radiation from a treatment head;
   modulating the primary photon beam with a plurality of jaws and a multi-leaf collimator (MLC) comprising a plurality of leaves through movement of the plurality of jaws and the plurality of leaves, the movement being expressed as a plurality of control points;
   organizing a plurality of jaw-opening positions corresponding to relative positions of the plurality of jaws and represented by the plurality of control points into a plurality of jaw-opening sets;
   deriving a three-dimensional (3D) head scatter fluence for each jaw-opening set in the plurality of jaw-opening sets; and
   combining 3D fluences of the plurality of jaw-opening sets to derive a 3D fluence of the scattered radiation from the treatment head.

2. The method according to claim 1, wherein the primary photon beam is generated by a medical linear accelerator (linac).

3. The method according to claim 1, wherein a JOS of the plurality of jaw-opening sets comprises a group of proximately disposed jaw-openings.

4. The method according to claim 1, wherein each JOS of the plurality of jaw-opening sets comprises a representative jaw-opening of a plurality of jaw-openings.

5. The method according to claim 4, wherein a representative jaw-opening is calculated as an arithmetic average of the jaw openings comprised in the JOS.

6. The method according to claim 4, wherein deriving the 3D fluence corresponding to a JOS of the plurality of jaw-opening sets comprises:
   calculating a two-dimensional (2D) opening ratio matrix (ORM) corresponding to the JOS;
   determining the representative jaw-opening corresponding to the JOS; and
   deriving a three-dimensional (3D) fluence corresponding to the JOS from the representative jaw-opening and the 2D ORM corresponding to the JOS.

7. The method according to claim 6, wherein the calculating a 2D ORM corresponding to a JOS comprises:
   referencing the MLC to determine positions of the plurality of leaves for the plurality of control points; and
   determining an opening ratio matrix (ORM) corresponding to the JOS from the positions of the plurality of leaves.

8. The method according to claim 7 wherein the determining the ORM corresponding to the JOS comprises referencing a full leaf sequence for the RT, the full leaf sequence comprising positions of the plurality of leaves.

9. The method according to claim 7, wherein determining the ORM corresponding to the JOS comprises approximating a partial ORM from a total primary ORM derived from the primary photon beam.

10. The method according to claim 9, wherein the total primary ORM comprises a plurality of pixels, each pixel of the plurality of pixels having a value.

11. The method according to claim 10, wherein the plurality of pixels is associated with the plurality of representative jaw-openings.

12. The method according to claim 11, wherein each JOS of the plurality of jaw-opening sets corresponds to a plurality of control points.

13. The method according to claim 12, wherein each JOS has an associated weight determined by a sum of monitor units of the control points corresponding to the JOS.

14. The method according to claim 13, wherein, the value of each pixel is distributed proportionally to a partial ORM for a JOS according to the number of monitor units associated with the JOS.

15. The method according to claim 14, wherein each pixel in the partial ORM of a JOS is associated with a proximity weight, the proximity weight decreasing exponentially as a function of the distance from a boundary of a space represented by a representative jaw-opening.

16. The method according to claim 15, wherein the proximity weight is equal to the value of one within the space represented by the representative jaw-opening.

17. The method according to claim 15, wherein, the value of each pixel of the total ORM is distributed to a partial ORM proportionally to the product of the MU weight and the proximity weight of the pixel.

18. A method of calculating head scatter phase space, the method comprising:

generating a primary photon beam, the primary photon beam producing scattered radiation from a treatment head of a medical linear accelerator;

modulating the primary photon beam with a plurality of jaws and a multi-leaf collimator (MLC) comprising a plurality of leaves through movement of the plurality of jaws and the plurality of leaves, the movement being expressed as a plurality of control points;

organizing a plurality of jaw-opening positions corresponding to relative positions of the plurality of jaws and represented by the plurality of control points into a plurality of jaw-opening sets;

deriving a plurality of distributions of directions corresponding to the plurality of jaw-opening sets; and deriving a total distribution of directions to represent head scatter phase space from the plurality of distribution of directions.

19. The method according to claim 18, wherein deriving a distribution of directions from the plurality of distributions of directions corresponding to a jaw-opening set of the plurality of jaw-opening sets comprises:

generating a particle in a planar head scatter source, the planar head scatter source located in the treatment head;

ray tracing the particle from the planar source through a representative jaw opening corresponding to the jaw opening set;

determining if a trajectory of the particle intersects with a jaw of the jaw opening set; and modifying a directional distribution at the position of the particle in response to determining that no intersection of the particle trajectory with a jaw of the representative jaw opening of the jaw opening set occurs.

20. A system for calculating three dimensional (3D) head scatter fluence of a radiation treatment beam, the system comprising:

a computer system having a processor coupled to a memory, the memory having computer readable code containing program instructions, the program instructions comprising:

instructions to generate a primary photon beam in a medical linear accelerator, the primary photon beam being modulated by a treatment head of the medical linear accelerator, the treatment head comprising a plurality of jaws and a multi-leaf collimator (MLC);

instructions to modulate the primary photon beam with the plurality of jaws and a plurality of leaves comprised in the MLC through movement of the plurality of jaws and the plurality of leaves, the movement being expressed as a plurality of control points;

instructions to organize a plurality of jaw-opening positions corresponding to relative positions of the plurality of jaws and represented by the plurality of control points into a plurality of jaw-opening sets;

instructions to derive a three-dimensional (3D) head scatter fluence corresponding to each jaw-opening set (JOS) of the plurality of jaw-opening sets; and instructions to combine the 3D fluences of the plurality of jaw-opening sets to derive an accurate 3D fluence of the head scattered radiation.

* * * * *